United States Patent
Kothandaraman et al.

(10) Patent No.: US 7,979,119 B2
(45) Date of Patent: Jul. 12, 2011

(54) DISPLAY GRAPHICS FOR USE IN STIMULATION THERAPIES

(75) Inventors: Sridhar Kothandaraman, Valencia, CA (US); John D. H. King, Los Angeles, CA (US); Carla M. Woods, Beverly Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1691 days.

(21) Appl. No.: 11/115,752

(22) Filed: Apr. 26, 2005

(65) Prior Publication Data

US 2006/0241721 A1   Oct. 26, 2006

(51) Int. Cl.
*A61N 1/00*   (2006.01)

(52) U.S. Cl. .......................................... 607/2

(58) Field of Classification Search .................. 600/513, 600/523; 607/2, 31, 28; 714/46, 800
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,208,008 A * | 6/1980 | Smith | 714/811 |
| 4,793,353 A | 12/1988 | Borkan | |
| 5,036,850 A | 8/1991 | Owens | |
| 5,167,229 A | 12/1992 | Peckham et al. | |
| 5,324,310 A * | 6/1994 | Greeninger et al. | 607/28 |
| 5,370,672 A | 12/1994 | Fowler et al. | |
| 5,447,164 A * | 9/1995 | Shaya et al. | 600/523 |
| 5,601,617 A | 2/1997 | Loeb et al. | |
| 5,626,629 A | 5/1997 | Faltys et al. | |
| 5,776,717 A | 7/1998 | Cao | |
| 5,800,473 A | 9/1998 | Faisandier | |
| 5,817,137 A | 10/1998 | Kaemmerer | |
| 5,893,883 A | 4/1999 | Torgerson et al. | |
| 5,938,690 A | 8/1999 | Law et al. | |
| 5,941,906 A | 8/1999 | Barreras, Sr. et al. | |
| 5,954,758 A | 9/1999 | Peckham et al. | |
| 6,052,624 A | 4/2000 | Mann | |
| 6,163,725 A | 12/2000 | Peckham et al. | |
| 6,308,102 B1 | 10/2001 | Sieracki et al. | |
| 6,381,496 B1 | 4/2002 | Meadows et al. | |
| 6,393,325 B1 | 5/2002 | Mann et al. | |
| 6,516,227 B1 | 2/2003 | Meadows et al. | |
| 6,587,724 B2 | 7/2003 | Mann | |
| 6,609,031 B1 | 8/2003 | Law et al. | |
| 6,609,032 B1 | 8/2003 | Woods et al. | |
| 6,622,048 B1 | 9/2003 | Mann et al. | |
| 6,662,053 B2 | 12/2003 | Borkan | |
| 6,718,210 B1 | 4/2004 | Peckham et al. | |
| 6,735,474 B1 | 5/2004 | Loeb et al. | |
| 2003/0114899 A1 | 6/2003 | Woods et al. | |
| 2003/0153959 A1 | 8/2003 | Thacker et al. | |

\* cited by examiner

*Primary Examiner* — George Manuel (57) ABSTRACT

Tissue stimulation systems, such as spinal cord stimulation systems, include a pulse generator to generate pulses at various amplitude, duration, and frequency through one or more electrodes. A visual depiction of both a pulse and an electrode configuration is thus provided herein. These depictions may be used in a stimulation display interface to readily convey stimulation parameter information to a user, wherein the interface is used in a stimulation session.

12 Claims, 6 Drawing Sheets

DISPLAY GRAPHICS FOR USE IN STIMULATION THERAPIES

BACKGROUND OF THE INVENTION

The present invention relates to tissue stimulation systems and more particularly to display interfaces having graphical depictions used during a stimulation session. One example of a stimulation system is a spinal cord stimulation system ("SCS"). Spinal cord stimulation is a well accepted clinical method for reducing pain in certain populations of patients. An SCS system typically includes an Implantable Pulse Generator (IPG) or a radio-frequency (RF) transmitter and receiver, electrodes, electrode leads, and when necessary, lead extensions. The electrodes are implanted along the dura of the spinal cord, and the IPG or RF transmitter generates electrical pulses that are delivered, through the electrodes, to the dorsal column and dorsal root fibers within the spinal cord. Individual electrode contacts (the "electrodes") are arranged in a desired pattern and spacing in order to create an electrode array. Individual wires within one or more electrode leads connect with each electrode in the array. The electrode leads exit the spinal column and attach to one or more electrode lead extensions, when necessary. The electrode leads or extensions are typically tunneled around the torso of the patient to a subcutaneous pocket where the IPG or RF-receiver is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical impulses to a plurality of electrodes. As another example, U.S. Pat. No. 3,724,467 issued Apr. 3, 1973 for "Electrode Implant For The Neuro-Stimulation of the Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes, which are positioned longitudinally on the spinal cord. Electrical pulses applied to the electrodes block perceived intractable pain, while allowing passage of other sensations. A patient operated switch allows the patient to adjust the stimulation parameters.

An SCS system treats chronic pain by providing electrical stimulation pulses through the electrodes of an electrode array located at the distal end of a lead placed epidurally next to a patient's spinal cord. The combination of electrodes used to deliver stimulation pulses to the targeted tissue constitutes an electrode configuration. In other words, an electrode configuration represents the polarity, being positive, negative, or zero and relative percentage of the current or voltage provided through each of the electrodes.

Electrode arrays used with known SCS systems may employ between 1 and 16 electrodes on a lead. Electrodes are selectively programmed to act as anodes, cathodes, or left off, creating an electrode configuration. The number of electrodes available, combined with the ability to generate a variety of complex stimulation pulses, presents a huge selection of electrode configurations and stimulation parameter sets to the clinician. When an SCS system is implanted, a procedure is performed to select one or more effective electrode configurations and stimulation parameter sets for a particular patient. Such a session of applying various stimulation parameters and electrode configurations may be referred to as a "fitting" or "programming" session. Additionally, a series of electrode configurations to be applied to a patient may be organized in a steering table or in another suitable manner.

Other parameters that may be controlled or varied in SCS are the frequency of pulses provided through the electrode array, pulse width, and the strength (amplitude) of pulses delivered. Amplitude may be measured in milliamps, volts, etc., as appropriate, depending on whether the system provides stimulation from current sources or voltage sources. With some SCS systems, the distribution of the current/voltage across the electrodes (including the case of the pulse generator or receiver, which may act as an electrode) may be varied such that the current is supplied via numerous different electrode configurations. In different configurations, different combinations of electrodes may provide current (or voltage) in different relative percentages of positive and negative current (or voltage). Moreover, there may be some electrodes that remain inactive for certain electrode configurations, meaning that no current is applied through the inactive electrode.

Previous SCS technology identified these parameters and effectuated stimulation through an electrode array using specific electrode configurations. These parameters, including distribution (if available), configuration, strength, pulse width, etc., are programmed after implantation in a "fitting" procedure. During the fitting, an extremely large number of possible combinations of stimulation parameters may be tested.

In order to test the effectiveness on a particular patient of various stimulation parameters and electrode configurations, it is necessary to provide a series of stimulation parameters in a systematic method. Several such systems exist including the systems disclosed in U.S. Pat. No. 6,393,325, herein incorporated by reference in its entirety, wherein a patient may direct the movement of the stimulus current through a suitable interface.

During a programming session, a clinician and a patient may use a display screen, such as the one described in U.S. Pat. No. 6,622,048, herein incorporated by reference in its entirety. Such a display screen may include a depiction of the human figure divided into body regions.

Other display graphics may be developed to make the programming efficient, easy, and accurate and to readily convey the values of stimulation parameters to a clinician and patient. There is a need to display the different electrodes of the array and to depict the electrodes as an anode or a cathode and to depict any current distribution among the implanted electrodes. Displays also should graphically convey the applied relative values of amplitude, pulse width and pulse rate. Such display graphics are described herein, such as icons for electrode configurations and pulse parameters. These graphics convey information regarding the values of the stimulation parameters and electrode configurations in an easily understood graphical format.

SUMMARY OF THE INVENTION

One embodiment of the invention is a system for programming a tissue stimulation apparatus having a plurality of electrodes implanted in a patient, wherein the apparatus delivers stimulation pulses having a pulse amplitude, a pulse width and a pulse rate to the patient's tissue through at least one of the electrodes.

The system includes at least one graphical display of the applied stimulation pulse. The graphical display of the applied stimulation includes a pulse waveform, wherein a relative height of the pulse waveform may correspond to the pulse amplitude of the applied stimulation pulses, wherein a relative width of the pulse waveform may correspond to the pulse width, and wherein the pulse waveform may be sequentially displayed at a plurality of locations on the graphical display for a variable interval of time, wherein the interval of time may correspond in a generally inverse fashion to the pulse rate. Pulse rate may be depicted by moving the waveform through a plurality of locations in, for example, a horizontal pattern, wherein the pulse waveform moves (e.g., from left to right) across the graphical display at a rate generally proportional to the stimulation pulse rate.

Other features of the graphical display may include a numerical value of the pulse amplitude, pulse width, and pulse rate. The user interface of the stimulation system may include a user interface that has a plurality of these graphical displays of applied stimulation. Each of the graphical displays may correspond to a channel or to an area of the body, to be programmed. One of the plurality of graphical displays may be indicated on the user interface as a particular channel that is being programmed by at least one of a color, a shape, a chart, a graph, a pattern, one or more words, and one or more symbols. In a similar regard, one of the plurality of graphical displays may be inactive or not currently selected for programming. Such information may be conveyed to a user by a color, a shape, a chart, a graph, a pattern, one or more words, and one or more symbols.

Another embodiment is a graphical display that may depict polarity and/or relative current distribution for each of the implanted electrodes. This graphical display may also be incorporated into a tissue stimulation system. The graphical display of the implanted electrodes may include a plurality of icons, wherein each icon corresponds to each implanted electrode and each icon has a plus sign, a minus sign, or a null or no sign, wherein the sign indicates the polarity of each electrode. Alternatively, the graphical display may include an icon corresponding to each active electrode, while inactive electrodes are not displayed (instead, a blank area may appear where the icon would otherwise appear) or are displayed in as a faded, inactive icon.

Each icon may also or instead have a numerical value between, for example 0 and 100 or between −100 and 100, wherein the numerical value represents a relative current distribution or polarity percentage of each electrode. Relative current distribution of each electrode may also be depicted by a shape, a chart, a graph, a pattern, one or more words, and one or more symbols. One or more of these icons may have a different color, such as red, than the other icons, wherein different colors may indicate a high impedance state, polarity, polarity percentage (relative current distribution), etc., for the corresponding electrode. Impedance values may also be depicted by one or more colors, shapes, charts, graphs, patterns, words, and symbols.

BRIEF DESCRIPTION OF THE DRAWINGS

The above and other aspects of the present invention will be more apparent from the following more particular description thereof, presented in conjunction with the following drawings wherein.

DETAILED DESCRIPTION OF THE INVENTION

It is to be understood that this invention is not limited to the particular devices, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to an "electrode" is a reference to one or more electrodes and equivalents thereof known to those skilled in the art, and so forth. Unless defined otherwise, all technical and scientific terms used herein have the same meanings as commonly understood by one of ordinary skill in the art. Although any methods, devices, and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

Graphical displays are herein described for use in a stimulation system. These displays may be included in any suitable interface, such as a display screen, a handheld device, a monitor, a laptop, a PDA, a joystick, or any such device. The displays may be interactive, such as a touch screen, or may be simply informative. A pulse and/or an electrode configuration may be depicted in the present embodiments. The graphical displays may be used as part of a stimulation system or related devices to convey stimulation parameters to a user, such as during the fitting or programming of the stimulation system.

A pulse generator generates pulses having an amplitude, duration and frequency. During stimulation and/or programming, it may be useful for a user to be able to make selections of parameters that are useful in meeting the therapeutic objectives. Additionally, being able to change and evaluate stimulation parameters may be helpful. Therefore, having a visual representation of the applied stimulation pulses is desirable. Active electrodes of the electrode array may receive a current or voltage pulse having a selected amplitude, pulse width, and repetition frequency. A pulse may be graphically represented, such as the graphs seen in FIGS. 1-6.

Figure 1:
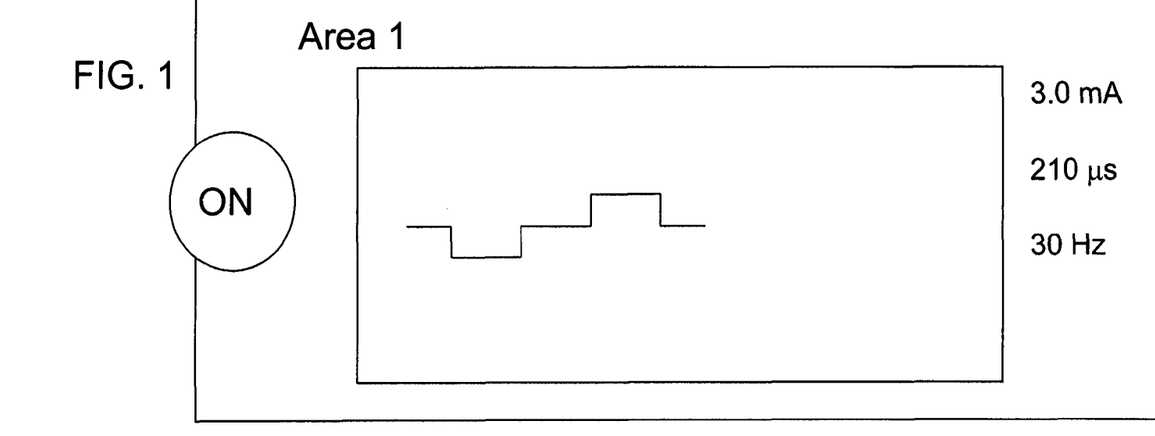
FIG. 1 depicts a front view of a portion of a display screen representing a biphasic pulse at a certain amplitude and at a certain pulse width at position 1.
Figure 2:
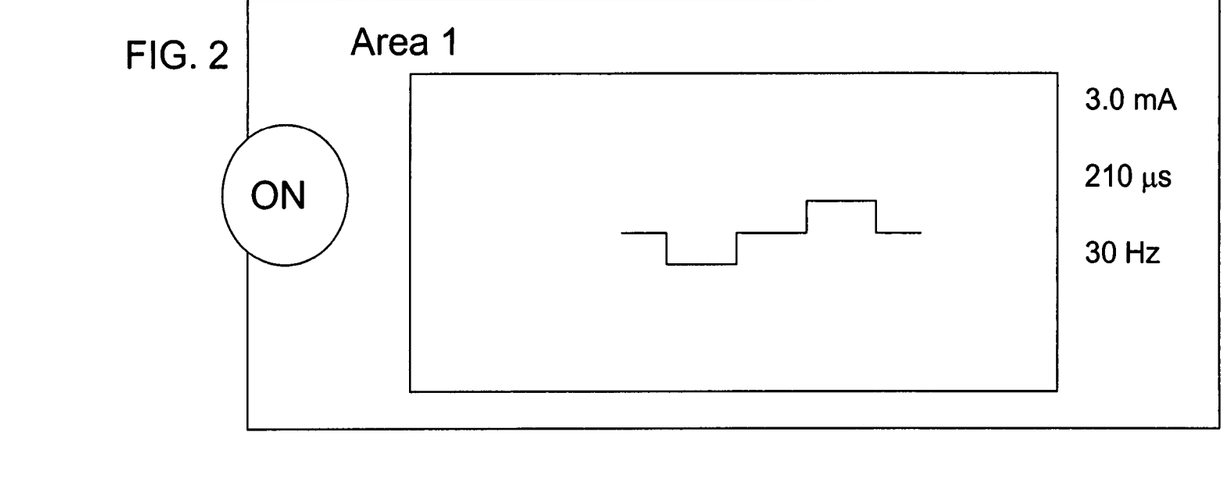
FIG. 2 depicts a front view of a portion of a display screen representing the pulse represented in FIG. 1 at position 2.
Figure 3:
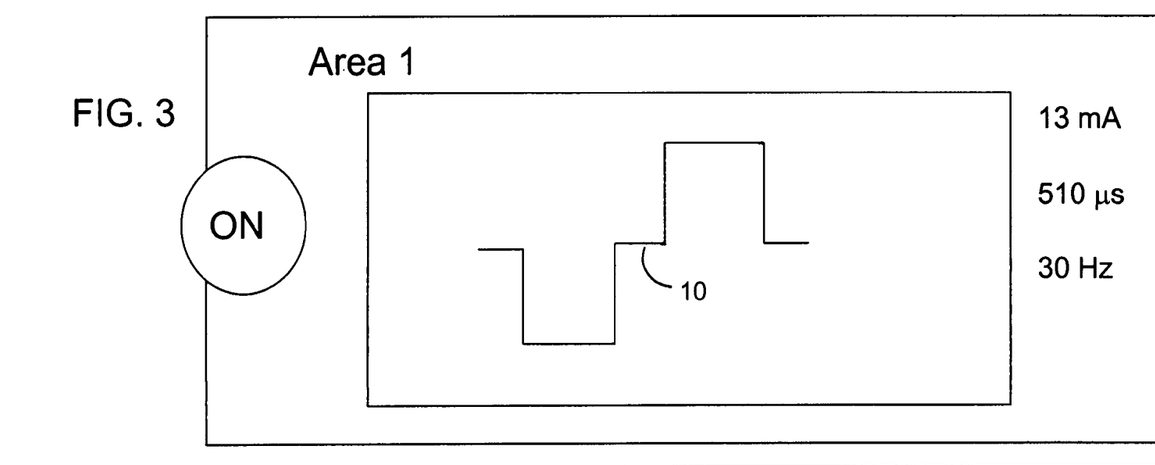
FIG. 3 depicts a front view of a portion of a display screen representing a pulse at a higher amplitude and wider pulse width than the pulse depicted in FIG. 1.

A graphical display of a pulse may include a line or a waveform. The depiction of a pulse may be a square biphasic waveform, i.e., a line extending in a symmetrical pattern above and below a hypothetical x-axis and y-axis of the display, such as the wave forms displayed in FIGS. 1 and 2. A height of the waveform may represent a pulse amplitude, while a total length (width) of the waveform may represent a pulse width. Pulse width is synonymous with pulse duration. For example, the pulse amplitude of the pulse illustrate in FIG. 1 is 3.0 mA, which is depicted with a waveform having a relatively small height. FIG. 3, by contrast, has a pulse amplitude of 13 mA, illustrated by a waveform having a relatively larger height. In FIG. 1, the pulse has a pulse width of 210 µs, which is illustrated by a relatively narrow waveform. In FIG. 3, the pulse has a pulse width of 510 µs, which is illustrated by a relatively wider waveform. Therefore, the y-axis of the display represents the amplitude of the current pulse, while the x-axis is time, dividend into increments of, for example, 1 millisecond.

The shape of the pulse waveform may depend on the type of pulse generated by the pulse generator in the stimulation system. The waveform may be biphasic or multiphasic, meaning that it may have two or more phases. The first phase of the biphasic pulse represents the stimulation pulse supplied by the electrodes in the stimulation system. The second phase of the biphasic waveform represents the recharge phase as more fully described in U.S. Pat. No. 6,516,227, incorporated herein by reference. During the recharge phase, current sources may be turned OFF, and the stimulus current results from a passive recharge or redistribution of the charge flowing from the coupling capacitance present in the stimulus circuit. Alternatively, an active recharge phase may be employed. A symmetrical active biphasic current pulse represented by the waveforms illustrated in FIGS. 1 and 2 represents a balanced charge condition. In other words, the first and second phases have the same total area (height multiplied by width).

Figure 1A:
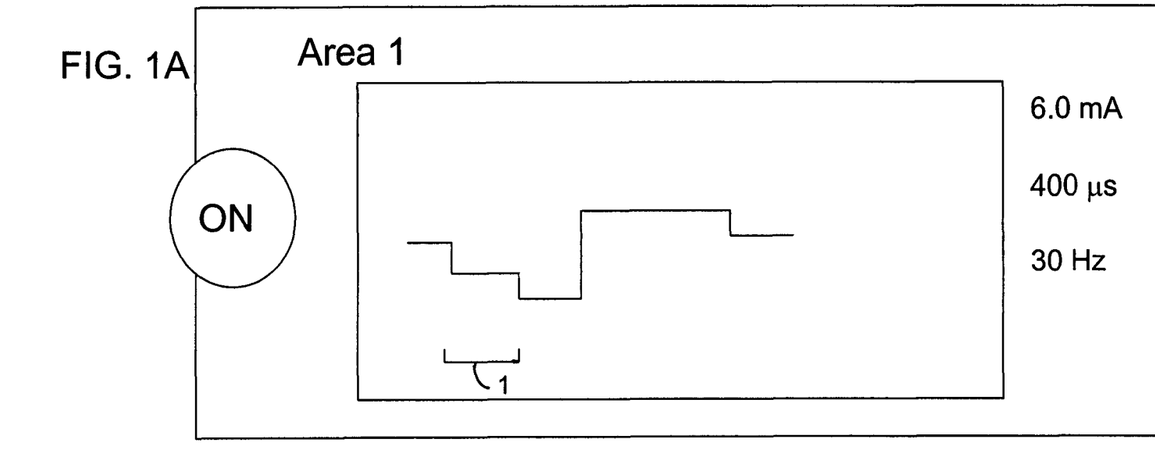
FIG. 1A depicts of a portion of a display screen representing a multiphasic pulse.
Figure 1B:
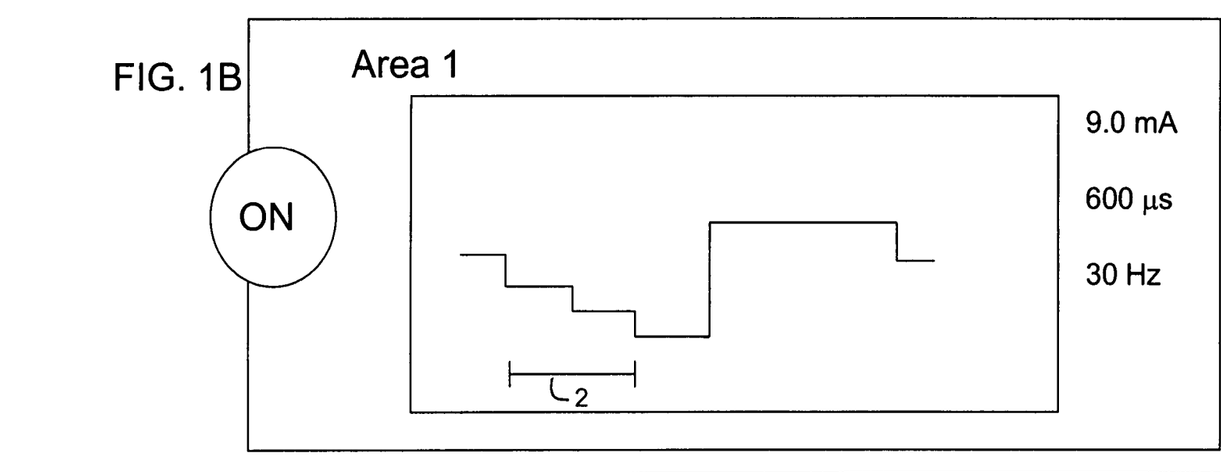
FIG. 1B depicts of a portion of a display screen representing a multiphasic pulse.

As stated above, the waveform may represent a multiphasic pulse, such as the ones displayed in FIGS. 1A and 1B. An example of a multiphasic pulse is one that incorporates a "pre-pulse" phase in addition to the stimulation and recharge phases. A "pre-pulse" is a sub-threshold stimulus with a duration that is usually several hundred microseconds in duration and precedes the stimulus pulse. As seen in FIG. 1A, a depolarizing pre-pulse [1] may be delivered. FIG. 1B shows a pulse with a two-step sub-threshold pre-pulse [2].

While a separate waveform for each electrode of the array may be displayed, FIGS. 1-3 represent a total or aggregate stimulation pulse being applied to the array. Some of the individual electrodes may not be active in the array. As explained in U.S. Pat. No. 6,516,227, if an electrode is a cathode, the waveform may be drawn below the x-axis, while if the electrode is an anode, the waveform may be drawn above the x-axis. Since FIGS. 1-3 represent a total or aggregate stimulation pulse being applied to the array, the waveforms are arbitrarily displayed as "cathodes," since the waveforms originate below the x-axis. Alternatively, the waveforms could originate above the x-axis (not shown).

There may also be an inter-phase period between phases, such as between the first phase (stimulus pulse) and the second phase (recharge pulse). This inter-phase period is illustrated as a horizontal line [10] in FIG. 3. The inter-phase period 10 may be between about 1 and about 100 microseconds, for example. The pulse generator may be programmed in an active or passive recharge mode (second phase). The square, biphasic pulse waveforms shown in FIGS. 1-3 correspond to a system programmed in active recharge mode, wherein the recharge pulse is the same height and width as the stimulation pulse.

Figure 3A:
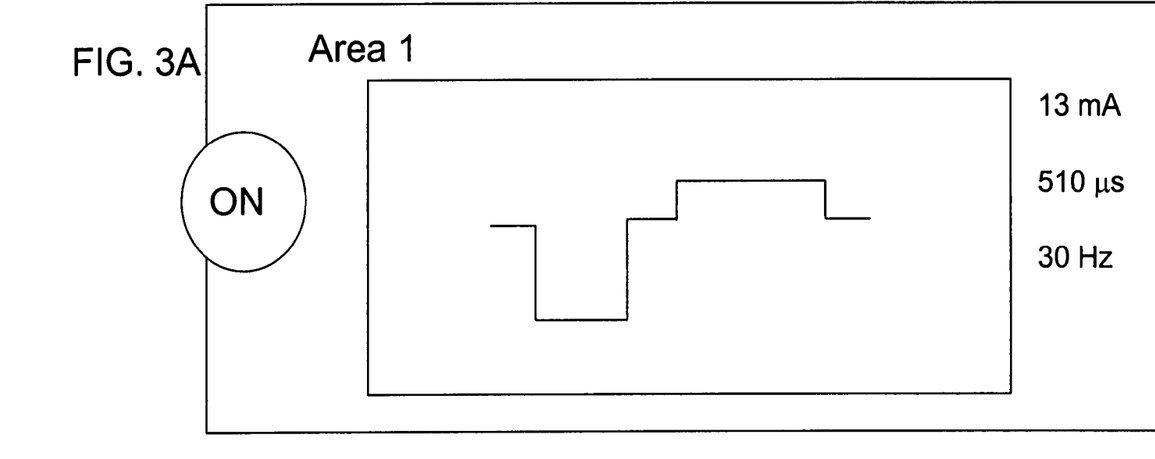
FIG. 3A depicts a front view of a portion of a display screen representing a pulse having the same amplitude and pulse width, during the stimulation phase, as in FIG. 3, but with the active recharge phase being longer in duration than the stimulation phase.
Figure 3B:
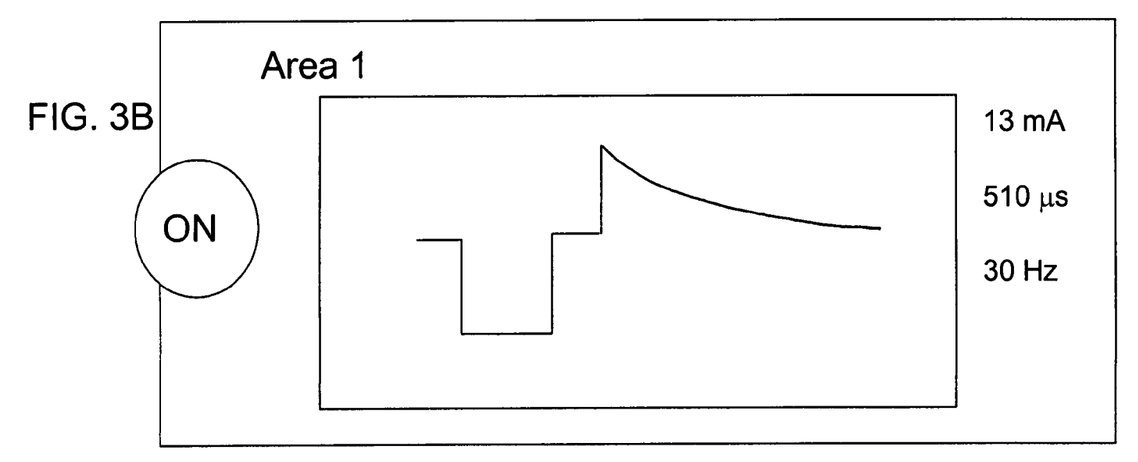
FIG. 3B depicts a front view of a portion of a display screen representing a pulse having the same amplitude and pulse width, during the stimulation phase, as in FIG. 3, but with a passive recharge phase.

If the recharge pulse were programmed to have a different pulse width than the stimulation pulse, the second phase of the waveform shown in FIG. 3 could be narrower or wider and taller or shorter, corresponding to the characteristics of the recharge pulse. For example, the waveform shown in FIG. 3A illustrates an active recharge phase that is shorter and wider than the stimulus pulse (first phase). However, the two phases of FIG. 3A have the same total area (height multiplied by width or amplitude multiplied by duration). Alternatively, if the pulse generator is programmed in a passive recharge mode, the second phase of the waveform in FIG. 3 may be shown as a curved line, corresponding to the amplitude of the passive recharge phase decreasing over a period of time. See FIG. 3B illustrating a passive recharge mode. As seen in FIGS. 3, 3A and 3B, each of the first phase stimulation pulses illustrated has the same amplitude, pulse width, and pulse rate. However, the recharge phase is different in each case, as readily observed by a clinician programming the stimulation system. Any shapes, other graphical means or other means (such as color, or numerical or text entries) that convey information about the characteristics of the pulse waveform may be used to provide additional information to the user.

Pulse frequency may also be graphically illustrated in that the waveform may "move" across the screen in proportion to the stimulation pulse frequency (rate). For example, FIG. 1 shows a pulse at a first position on the screen, while FIG. 2 shows a pulse at a second position. This depiction of the same pulse at "n" different consecutive locations across the screen displayed during a certain time interval may represent pulse frequency. This relative motion of the pulse waveform across the display screen may be inversely proportional to the applied stimulation pulse rate. Therefore, a higher pulse rate may be graphically illustrated by moving the pulse through n different locations in a relatively short time, compared to a lower pulse rate. For example, the pulse rate in FIGS. 1-3 is 30 hertz, which may be a relatively low value, in which case the pulse would move relatively slowly from left to right, along a horizontal path across the user's display screen.

FIG. 1 depicts a portion of a display screen representing a pulse at a certain amplitude and at a certain pulse width at a first position. FIG. 2 depicts a portion of a display screen representing a pulse at a second position, having the same amplitude and pulse width as the pulse represented in FIG. 1. FIG. 3 depicts a portion of a display screen representing a pulse at a higher amplitude and wider pulse width than the pulse depicted in FIG. 1. As seen in FIGS. 1-3, any number of pulse waveforms may be employed to visually represent pulses to a user.

In a typical stimulation session, pulse amplitude may range from about 1 milliamp to about 13 milliamps or more, depending on the system. The pulse width may be from about 10 μs to about 1000 μs or more. The frequency may be from about 2 hertz to about 1200 hertz or more. These values of pulse amplitude, pulse width and pulse frequency may be displayed in the graphical depiction in any manner. For example, in FIGS. 1-6, the three values are displayed numerically in a column that runs along the right-hand-side of the screen. The displayed value of the pulse width corresponds to the stimulation phase of the pulse.

Figure 4:
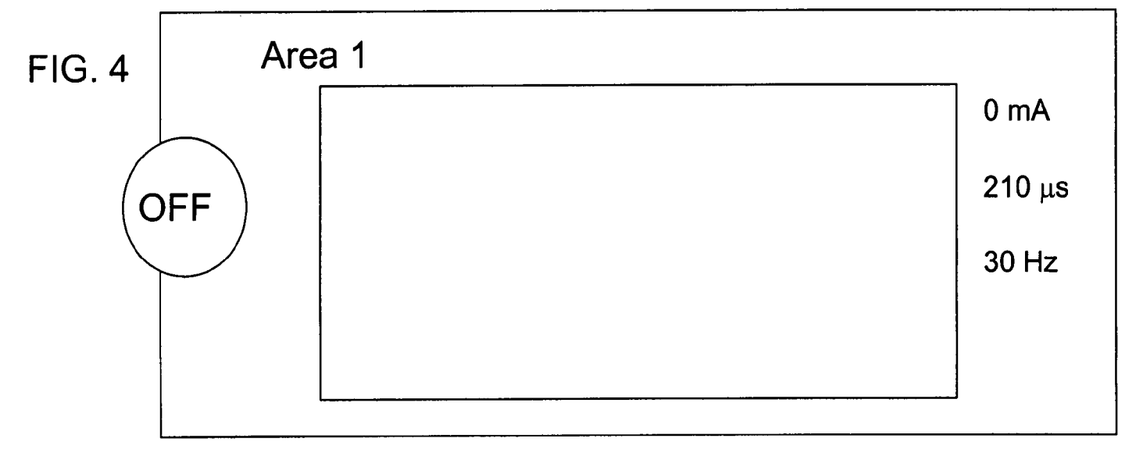
FIG. 4 depicts a front view of a portion of a display screen representing a pulse generator that is OFF (i.e., with no amplitude).

On the graphical depiction, a button may reveal if the pulse generator is ON or OFF. For example, in FIGS. 1-3, the pulse generator is ON, as shown in the button on the left hand side. Any suitable indicator may be used. In FIG. 4, the pulse generator is OFF, as represented by the button on the left. This button may be a color, a shape, a chart, a graph, a pattern, one or more words, and one or more symbols, sufficient to indicate whether the Area is ON, OFF, or not selected for programming.

Additionally, there may be more than one graphical or other depiction on a user's display interface at once. For example, there may be four (4) graphical depictions of pulses, one that corresponds to each area of the body to be stimulated. Therefore, an appropriate label such as "Area 1", "Area 2," "Area 3" and "Area 4" may be used to distinguish between the different pulses being applied to different areas of the body. These areas may be referred to as "channels." In U.S. Pat. No. 6,393,325, a programming session uses one or more channels corresponding to a body area being stimulated. For example, channel 1 comprises stimulation pulses applied to, or felt in, the right leg; while channel 2 comprises stimulation pulses applied to, or felt in, the left leg. After the user has selected the "best" selection of stimulation parameters for the given channel, he or she is offered the choice to program additional channels. Therefore, one or more channels may be highlighted (i.e., with some indicator of the active channels) on the screen, while other channels that are not programmed remain faded or with values of zero and no waveform or some other indication. Such channel depiction may be used in connection with a graphical representation of the human figure. For example, if a channel is being programmed for the right leg, a graphical display of the pulse being supplied may be displayed, such as FIGS. 1-3, while a human figure with the right leg highlighted (i.e., with some type of area indicator) is also displayed on the user interface.

Figure 5:
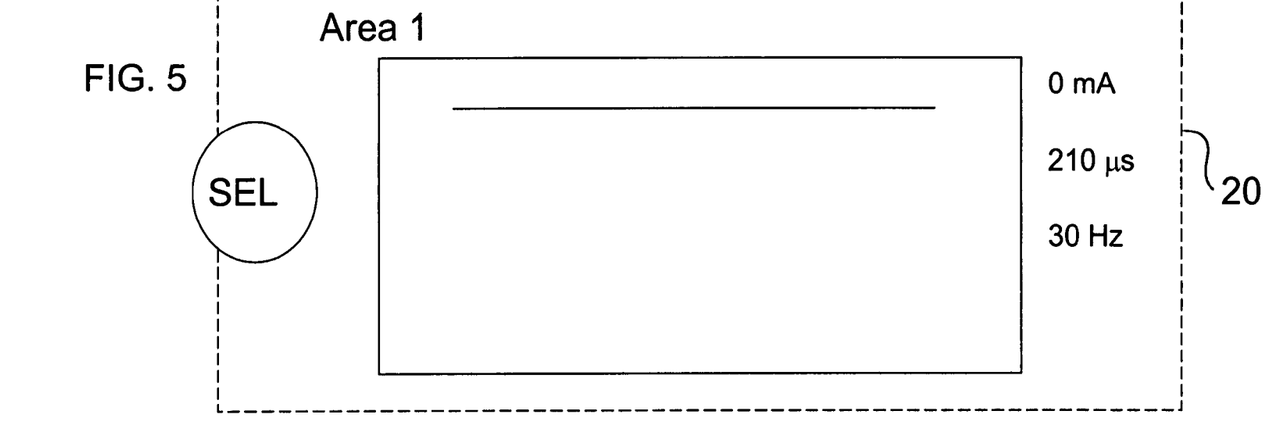
FIG. 5 depicts a front view of a portion of a display screen representing that "Area 1" of the pulse generator is not selected or in use.
Figure 6:
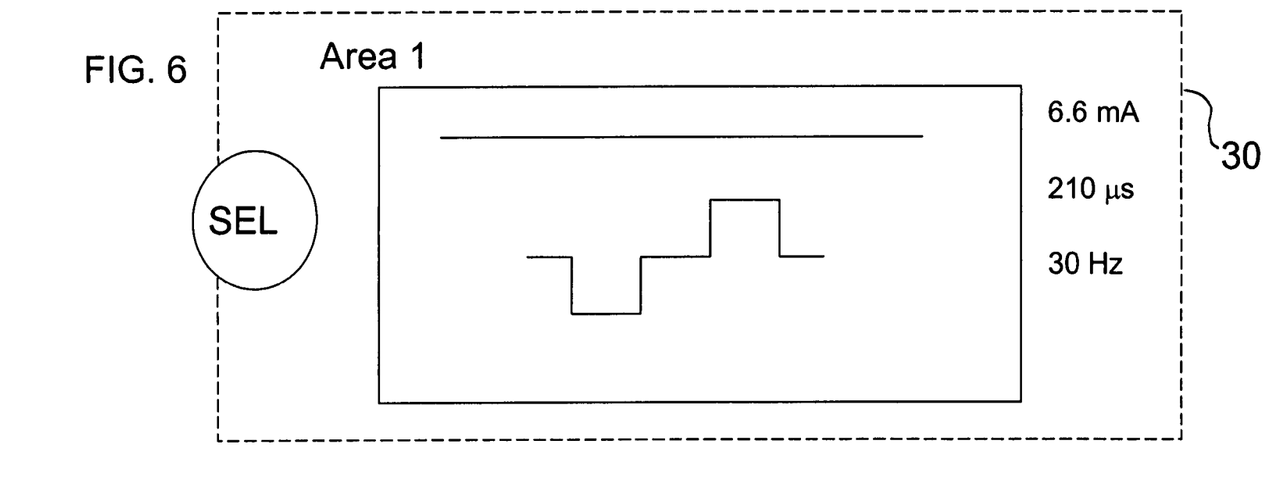
FIG. 6 depicts a front view of a portion of a display screen representing that "Area 1" of the pulse generator is not selected, but is in use.

FIG. 5 represents a channel that may be selected to be programmed. However, the pulse generator is not supplying any stimulation to the channel represented in FIG. 5 (no pulse waveform is shown on the display). By contrast, FIG. 6 represents the display for an area or channel that is may be selected for programming and is supplying stimulation to the channel represented in the figure. Because it is not currently selected for programming, FIG. 5 may be shown, for instance, as faded in color, with thinner lines, or the like, depicted in FIG. 5 as a dashed line [20]. To program the area represented by FIG. 5, the user can select this display by any appropriate means, such as by using a mouse to click on the "SEL" button on the left portion of the display. As mentioned above, FIG. 6 represents the display for an area that is ON, and generating a pulse at a particular amplitude and width, as represented by the biphasic waveform. However, the area represented in FIG. 6 is not currently selected for programming by the user, as indicated by the dashed line [30] in FIG. 6, which represent a faded area, thin lines, or the like.

Each of the graphical displays may correspond to a channel, or to an area of the body, to be programmed. One of the plurality of graphical displays may be indicated on the user interface as a particular channel that is being programmed, such as FIG. 3, by at least one of a color, a shape, a chart, a graph, a pattern, one or more words, and one or more symbols. In a similar regard, one of the plurality of graphical displays may not be currently selected for programming, such as FIGS. 5 and 6. Such information may be conveyed to a user by a color, a shape, a chart, a graph, a pattern, one or more words, and one or more symbols.

In addition to stimulation pulses, electrode configurations may be graphically represented. As used herein, an "electrode configuration" refers to a polarity and/or to a relative distribution of current or voltage applied through the electrodes of the electrode array. Electrodes may be positive, negative, or turned off, such that a subset of anodes and cathodes are created within the electrode array. A polarity of each electrode may be a positive or negative "1" or a fraction thereof. For example, one electrode of the electrode array may have a polarity of negative "1" (cathode), while another electrode may have a polarity of positive "1" (anode). Additionally, in some stimulation systems, a polarity may be spread out among different electrodes, such that one electrode has a polarity of +0.5, while another has −0.5. This distribution is known as polarity "distribution" or "percentages" among the electrodes of an electrode array. Therefore, for such systems, each electrode configuration also represents a polarity percentage of each active electrode of an electrode array. In the above examples, if an electrode has a polarity of negative one (−1), it is a cathode with 100% of the cathodic current distribution. If an electrode has a polarity of 0.5, it is an anode with 50% of the anodic distribution. Thus, a numerical value may be easily associated with a polarity distribution.

The total current applied through each electrode may be about 1 to about 13 milliamps, up to a "grand total" of 20 milliamps applied through all active electrodes combined. The values of the electrode configuration therefore represent a percentage of this grand total current applied through an individual electrode. Alternatively, the stimulation may be measured by voltage applied to the electrodes.

During a stimulation session, it may be helpful for a user to know whether a particular electrode of the electrode array is operating as an anode, a cathode, or is turned OFF. It may also be important for the user to know what percentage of the current (or voltage) is being applied through a particular electrode, when applicable. Such knowledge allows a user to evaluate and/or to change the electrode configurations being applied in order to meet therapeutic objectives. Therefore, the designs of one or more of FIGS. 7-18 could be incorporated into a stimulation display interface.

Icons representing an electrode may include two main features: (1) a depiction of either a plus or minus sign, wherein the plus sign represents an anode and wherein the minus sign represents a cathode, for example, and (2) a numerical value or equivalent associated with the sign, wherein the numerical value or equivalent represents a percentage of current (or voltage) distribution. The numerical value may range from 0 to 100 or from −100 to +100, thus representing the percentage of current (or voltage) being supplied to that particular electrode. Equivalents to the numerical value may include charts, such as pie charts, or graphs, such as bar graphs, depicting percentages.

Furthermore, the display may also include the use of one or more colors to represent one or more characteristics of the particular electrode. For example, polarity may be shown with colors, instead of, or in addition to positive and negative signs. As another example, various colors may be used to indicate that a particular electrode has a high or low impedance value. Impedance (defined as voltage divided by current) may be used as a measure of system stability and hardware connectivity. For a spinal cord implantation, the electrode impedance will typically range between about 400 ohms and 1000 ohms. Implanted electrical stimulation systems (including leads and electrodes) convey electrical pulses of known energy to the target tissue to be excited. The target tissue represents a known electrical load into which the electrical energy associated with the stimulation pulse is to be delivered. If the impedance is too high, a connector and/or lead that connects with the electrode may be open or broken. If the impedance is too low, there may be a short circuit somewhere in the connector/lead system. In either event (too high or too low impedance), the system may be unable to perform its intended function. Impedance measurement and its importance in stimulation systems are more thoroughly detailed in U.S. Pat. No. 6,516,227, herein incorporated by reference in its entirety.

As another example, other display indicators may be used to show polarity and/or polarity percentages, and/or impedance, such as various colors, charts, graphs, shapes, patterns, symbols, words or the like. For example, a pie chart or bar chart may be used to show the percentage of the polarity of each electrode. As another example, an electrode having a high impedance value may have an overlaying pattern associated with its icon such as a line grid. As another example, an icon may include the letter "i" to indicate that the electrode has a high impedance value. Other examples may be readily ascertained by one skilled in the art.

Thus, for example, the color red may be used to indicate that an electrode has a high impedance value. A lighter shade of red or a different color may be used to represent a low impedance. The numerical value of the impedance may also be shown. If an electrode has too high or low an impedance value, a fitting program may automatically block the supply of current (or voltage) to this electrode. The high or low impedance indicator alerts the user to avoid the particular electrode(s) or that the system is avoiding the electrode(s).

Figure 7:
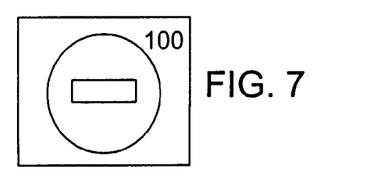
FIG. 7 depicts a front view of a portion of a display screen representing an electrode as a cathode with 100% current distribution.

FIG. 7 depicts a front view of a portion of a display screen representing an electrode as a cathode with 100% current distribution. This example design is generally a square/rectangular shaped icon including a sign and a numerical value. This design informs a user that this particular electrode is acting as a cathode and that this electrode is the only cathode in the array at this time. This information is readily interpreted by the user through the use of the minus sign and the numerical value of 100. As explained above, the numerical value may instead be represented by a chart or graph, such as a pie chart.

Figure 8:
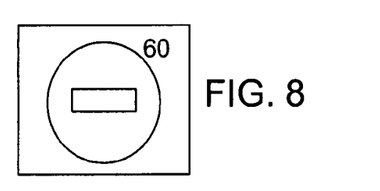
FIG. 8 depicts a front view of a portion of a display screen representing an electrode as a cathode with 60% current distribution.
Figure 17:
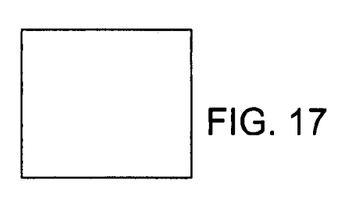
FIG. 17 depicts a front view of a portion of a display screen representing an electrode that has been turned OFF.

As another example, FIG. 8 represents an electrode as a cathode having 60% current distribution. This means that other electrodes in the array must comprise another 40% of the cathodic current being applied. Likewise, the icon of FIG. 8 conveys to a user that one or more other electrodes (or the pulse generator case or receiver) must be supplying the same amount of anodic current. Continuing this example, one electrode may supply 10% of the anodic current and a second electrode may supply 90%. Thus, the icon for the first would show a plus sign and the number 10, while the icon for the second would show a plus sign with the number 90. In this example, the other electrodes of the implanted array and potentially also the implanted case, if used as an electrode, would be shown as blank rectangles (such as shown in FIG. 17) or as icon with the numerical "0" and no plus or minus sign.

Each electrode of an electrode array and potentially also the implanted case may have a design featuring the electrode's polarity represented by a plus or minus sign or a null sign (such as a no sign, a zero sign, a color, a graph, a chart, and a shape) and/or numerical values (or other indicator, such as a chart or graph) representing the percentage current distribution. These depictions may be organized on a user interface in any suitable manner. For example, the electrode depictions may be arranged in sequential order, corresponding spatially to the electrode each represent. For two linear arrays of electrodes deployed in a parallel, side-by-side arrangement, the electrode array may be organized as two columns of these graphical rectangles, each indicating the plus or minus sign with the associated numerical value for polarity distribution.

Figure 9:
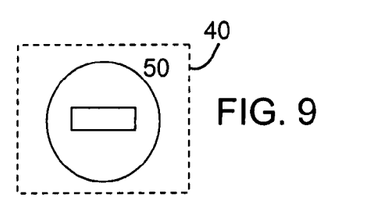
FIG. 9 depicts a front view of a portion of a display screen representing an electrode as a cathode with high impedance.
Figure 10:
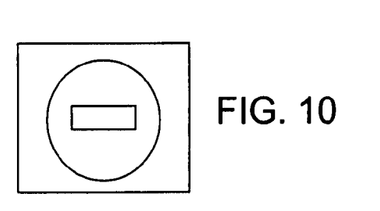
FIG. 10 depicts a front view of a portion of a display screen representing an electrode as a cathode without percent current distribution shown.
Figure 11:
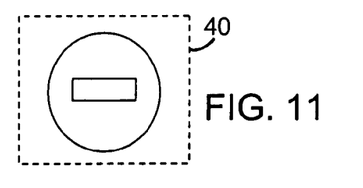
FIG. 11 depicts a front view of a portion of a display screen representing an electrode as a cathode without percent current distribution shown and with high impedance.

Additional examples are given as FIGS. 9-18. FIG. 9 depicts a portion of a display screen representing an electrode as a cathode with high impedance. As described earlier, to depict high impedance, the design may include the color red, depicted in FIGS. 9, 11, 14, and 16 as a dashed line framing the icon [40]. FIG. 10 depicts a minus sign alone, without indicating a numerical value. FIG. 11 depicts a portion of a display screen representing an electrode as a cathode without percent current distribution shown and with high impedance, as shown by dashed line [40].

Figure 12:
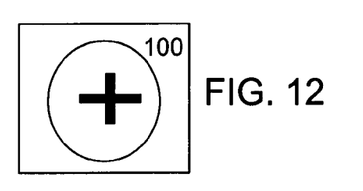
FIG. 12 depicts a front view of a portion of a display screen representing an electrode as an anode with 100% current distribution.
Figure 13:
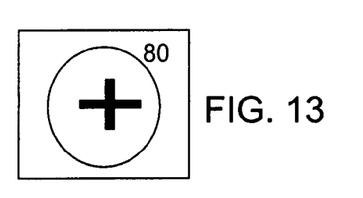
FIG. 13 depicts a front view of a portion of a display screen representing an electrode as an anode with 80% current distribution.
Figure 14:
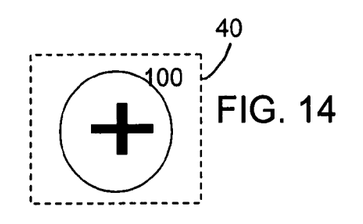
FIG. 14 depicts a front view of a portion of a display screen representing an electrode as an anode without percent current distribution and with high impedance.
Figure 15:
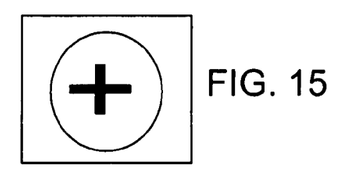
FIG. 15 depicts a front view of a portion of a display screen representing an electrode as an anode without current distribution shown.
Figure 16:
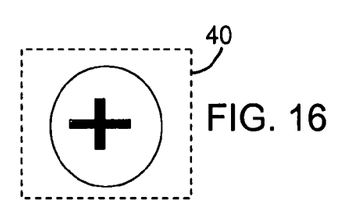
FIG. 16 depicts a front view of a portion of a display screen representing an electrode as an anode without current distribution shown and with high impedance.

FIG. 12 depicts a portion of a display screen representing an electrode as an anode with 100% current distribution. FIG. 13 depicts a portion of a display screen representing an electrode as an anode with 80% current distribution. FIG. 14 depicts a portion of a display screen representing an electrode as an anode without percent current distribution and with high impedance [40]. FIG. 15 depicts a portion of a display screen representing an electrode as an anode without current distribution shown. FIG. 16 depicts a portion of a display screen representing an electrode as an anode without current distribution shown and with high impedance [40].

Figure 18:
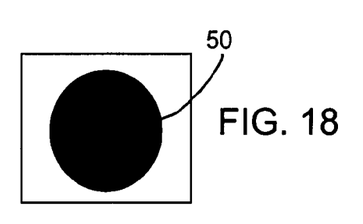
FIG. 18 depicts a front view of a portion of a display screen representing an electrode that has been turned OFF and having high impedance.

FIG. 17 depicts a portion of a display screen representing an electrode that has been turned OFF. Alternative to depicting this square icon as blank, a numerical value of "0" may be used to indicate that the electrode is turned OFF. FIG. 18 depicts a portion of a display screen representing an electrode that has been turned OFF and having high impedance [50], for instance, through using the color red. The display icon is simply a square with a circle included therein to show high impedance [50].

While the invention herein disclosed has been described by means of specific embodiments and applications thereof, numerous modifications and variations could be made thereto by those skilled in the art without departing from the scope of the invention set forth in the claims. For example, the methods discussed above are not limited to spinal cord stimulation systems and may be used with many kinds of stimulation systems such as cochlear implants, cardiac stimulation systems, peripheral nerve stimulation systems, brain stimulation systems and microstimulators.

What is claimed is:

1. A system for programming a tissue stimulation apparatus having at least one electrode implantable in a patient, wherein the apparatus is configured for applying electrical stimulation energy having a pulse amplitude, a pulse width and a pulse rate to the patient's tissue through the at least one electrode, the system comprising:
a user interface having a plurality of graphical displays configured for displaying a pulse waveform corresponding to the applied stimulation energy, wherein a height of the pulse waveform corresponds to the pulse amplitude and a width of the pulse waveform corresponds to the pulse width.

2. The system of claim 1, wherein each of the graphical displays corresponds to an area to be programmed.

3. The system of claim 2, wherein one of the plurality of graphical displays on the user interface is configured for indicating that a particular channel is being programmed by at least one of a color, a shape, a chart, a graph, a pattern, one or more words, and one or more symbols.

4. The system of claim 2, wherein one of the plurality of graphical displays on the user interface is configured for indicating that a particular area is inactive by at least one of a color, a shape, a chart, a graph, a pattern, one or more words, and one or more symbols.

5. The system of claim 2, wherein one of the plurality of graphical displays on the user interface is configured for indicating that a particular area is not being programmed by at least one of a color, a shape, a chart, a graph, a pattern, one or more words, and one or more symbols.

6. A system for programming a tissue stimulation apparatus having a plurality of electrodes implantable in a patient, wherein the apparatus is configured for applying electrical stimulation energy to the patient's tissue through the electrodes, the system comprising:
a graphical display configured for displaying a plurality of icons respectively corresponding to the implantable electrodes, and wherein each icon comprises a polarity sign indicating a polarity of the respective implantable electrode, and a polarity percentage sign indicating a polarity percentage of the respective implantable electrode.

7. The system of claim 6, wherein the polarity percentage sign comprises at least one of a numerical value, a chart, and a graph.

8. The system of claim 7, wherein the numerical value ranges between 0 and 100 or between −100 and 100.

9. The system of claim 6, wherein the polarity sign comprises at least one of a plus sign, a minus sign, a null sign, a color, and a shape.

10. The system of claim 9, wherein the null sign comprises at least one of a no sign, a zero sign, a color, a graph, a chart, a pattern, and a shape.

11. The system of claim 6, wherein the graphical display is configured for indicating an electrode with a high impedance state by at least one of a color, a shape, a chart, a graph, a pattern, one or more words, and one or more symbols.

12. The system of claim 6, wherein the tissue stimulation apparatus is a spinal cord stimulation system.

* * * * *